(12) United States Patent
Bang et al.

(10) Patent No.: US 9,074,134 B2
(45) Date of Patent: Jul. 7, 2015

(54) METHOD OF MANUFACTURING SOIL REINFORCED BY MICROBE-BASED BIO-BINDERS AND SOIL PRODUCED BY THE METHOD

(75) Inventors: Sang Chul Bang, Rapid City, SD (US); Sookie S. Bang, Rapid City, SD (US); Seong Rok Choi, Seoul (KR); Seok Jin Lee, Seoul (KR); Joo Ho Lee, Seoul (KR); Jong Sun Kim, Bucheon-si (KR)

(73) Assignees: LOTTE ENGINEERING & CONSTRUCTION (KR); ECHO PHILE (KR); SOUTH DAKOTA SCHOOL OF MINES AND TECHNOLOGY, Rapid City, SD (US)

(*) Notice: Subject to any disclaimer, the term of this patent is extended or adjusted under 35 U.S.C. 154(b) by 179 days.

(21) Appl. No.: 13/819,516

(22) PCT Filed: Nov. 10, 2011

(86) PCT No.: PCT/KR2011/008532
§ 371 (c)(1),
(2), (4) Date: Feb. 27, 2013

(87) PCT Pub. No.: WO2013/069830
PCT Pub. Date: May 16, 2013

(65) Prior Publication Data
US 2014/0238267 A1    Aug. 28, 2014

(51) Int. Cl.
| | |
|---|---|
| *C09K 17/42* | (2006.01) |
| *C09K 17/40* | (2006.01) |
| *C12N 1/20* | (2006.01) |
| *C04B 24/00* | (2006.01) |
| *C03C 15/00* | (2006.01) |
| *C12P 3/00* | (2006.01) |
| *C04B 26/00* | (2006.01) |
| *C04B 28/10* | (2006.01) |

(52) U.S. Cl.
CPC ............. *C09K 17/42* (2013.01); *C09K 17/40* (2013.01); *C12N 1/20* (2013.01); *C04B 24/00* (2013.01); *C03C 15/00* (2013.01); *C12P 3/00* (2013.01); *C04B 26/00* (2013.01); *C04B 28/10* (2013.01); *Y02W 30/97* (2013.01)

(58) Field of Classification Search
None
See application file for complete search history.

(56) References Cited

U.S. PATENT DOCUMENTS

| | | | | |
|---|---|---|---|---|
| 2008/0245272 | A1* | 10/2008 | Kucharski et al. | 106/638 |
| 2011/0027850 | A1* | 2/2011 | Crawford et al. | 435/168 |
| 2011/0262640 | A1* | 10/2011 | Dosier | 427/215 |

FOREIGN PATENT DOCUMENTS

| | | | |
|---|---|---|---|
| JP | 2010-275697 | * | 12/2010 |
| KR | 20030036593 | | 5/2003 |
| KR | 1020070093128 | | 9/2007 |
| KR | 1020110091552 | | 8/2011 |
| WO | 2006066326 | | 6/2006 |

OTHER PUBLICATIONS

International Search Report—PCT/KR2011/008532 dated Aug. 28, 2012.

* cited by examiner

*Primary Examiner* — Melvin C Mayes
*Assistant Examiner* — Colette Nguyen
(74) *Attorney, Agent, or Firm* — Cantor Colburn LLP

(57) ABSTRACT

The present invention relates to a method of manufacturing soil reinforced by microbe-based bio-binders and soil produced by the method. The bio-binders are not harmful to humans, do not cause environmental pollution and secure sufficiently the soil strength and resistance against wind. According to the method, the soil is prepared by binding sand whose major components are silica and alumina, ureolytic microbes, urea, calcium ion, and polymer fibers, and the content of polymer fibers in sand ranges from 0.05 wt % to 5 wt %. In addition, it is preferable that the microbes provide $CaCO_3$ at a rate at $1{\sim}7{\times}10^{-9}$ g $CaCO_3$ ppt $cell^{-1}$ $hr^{-1}$ under optimum conditions.

5 Claims, 2 Drawing Sheets

METHOD OF MANUFACTURING SOIL REINFORCED BY MICROBE-BASED BIO-BINDERS AND SOIL PRODUCED BY THE METHOD

TECHNICAL FIELD

The present invention relates to a method of manufacturing soil reinforced by utilizing microbes and soil produced by the method, more specifically, a method of manufacturing soil reinforced by high-strength bio-binders composed of urease-producing bacteria and polymer—synthetic or bio-degradable—fibers.

BACKGROUND ART

Ordinary binders that are widely used as binding hardeners of minerals in civil engineering works and construction sites contain limestone, clay, silica, etc. However, it is known that those are sometimes harmful to humans because toxicity remains even after construction, and components from the binders can cause various diseases such as atopy. In addition, civil engineering and construction wastes are common causes for environmental pollution these days. In order to remediate these problems, bio-binders using microbes, particularly, bacteria that can produce urease are described in this invention.

Bacteria, producing urease, have primarily been used to mediate the surface or the base of permeable materials. That is, bacteria have been used to treat oil or petroleum based pollutants, since the fluid velocity decreases as the permeability and porosity of permeable materials are reduced by the bacteria. On the other hand, the bio-binder based on urease-producing bacteria reduces the permeability and porosity through the formation of ammonia, a product of urea decomposition by urease. However, the existing bio-binders do not have enough strength to be used as materials for civil engineering structures and residential buildings.

Meanwhile, more than one third of the entire land on the earth is infertile arid land where trees and plants can hardly grow due to a little rainfall and a lot of evaporation. Also, the area of arid land is gradually expanding and desertification is a major reason for the expansion of arid land. In climatology, arid land means an area where precipitation is less than potential evapotranspiration. The potential evapotranspiration is the sum of evaporation from plants and evaporation from the ground when water is sufficiently supplied to the green area.

Desert soil representing arid land consists mostly of sand whose main components are silica and alumina. The binding strength of the soil is weak because of the inherent nature of sand, so desert soil presents too low strength to be used for road construction, and plants can hardly grow, since it can't retain enough water. In addition, topographical changes are severe because desert wind shifts sand and sandy dust phenomena become more and more frequent. Although attempts have been made in the past to improve the soil strength and wind resistance using microbe-based bio-binders, the strength and the resulting resistance against wind have not been sufficient enough for the binders to be applied to desert environment.

DISCLOSURE OF INVENTION

Technical Problem

The technical objective of this invention is to provide a method of manufacturing soil reinforced by microbe-based bio-binders that are not harmful to humans, do not cause environmental pollution, and secure sufficient soil strength and wind resistance, and to provide soil produced by the method.

Technical Solution

In order to manufacture the soil reinforced with microbe-based bio-binders to remediate the aforementioned technical problems, a sand whose main ingredients are silica and alumina is first prepared. Then, microbes that produce urease, urea, calcium ions, and polymer fibers are introduced to be bound to the sand. At this step, the content of the polymer fibers is 0.05 wt %~5 wt % of the sand. In addition, it is desirable that the microbes can form $CaCO_3$ at a rate of $1~7\times10^{-9}$ g $CaCO_3$ ppt cell$^{-1}$ hr$^{-1}$ under optimum conditions. Here, the polymer fiber is synthetic or bio-degradable fiber.

In the present invention, it is advised that the microbe be *Bacillus, Sporosarcina, Sporolactobacillus, Clostridium*, or *Desulfotomaculum, Sporosarcina pasteurii*, or their functional equivalents.

In the present invention, the polymer fibers can be bio-degradable fibers that are mineralized by depolymerization of the fibers. The bio-degradable fibers may be one of the following: Polylactic acid (PLA), Cellulose, rayon mixed with milk, fibers mixed with Chitosan, and rice straw. Fibers mixed with Chitosan or rice straw is preferred to the others, with the rice straw being the most preferable.

In the present invention, surface treatment of the sand may be also included after preparing the sand. Plasma or spraying method may be applied as a surface treatment, and the plasma may be performed under vacuum or atmospheric conditions. Also particles attached to the sand by the spraying method may be sand powder or functional particles.

Advantageous Effects

According to the method of manufacturing soil reinforced by microbe-based bio-binders and the soil produced by such method, soil that is not harmful to humans, doesn't cause environmental pollution, and secures sufficient soil strength and resistance against wind can be prepared by using urease-producing bacteria and polymer fibers.

BEST MODE FOR CARRYING OUT THE INVENTION

Figure 1:
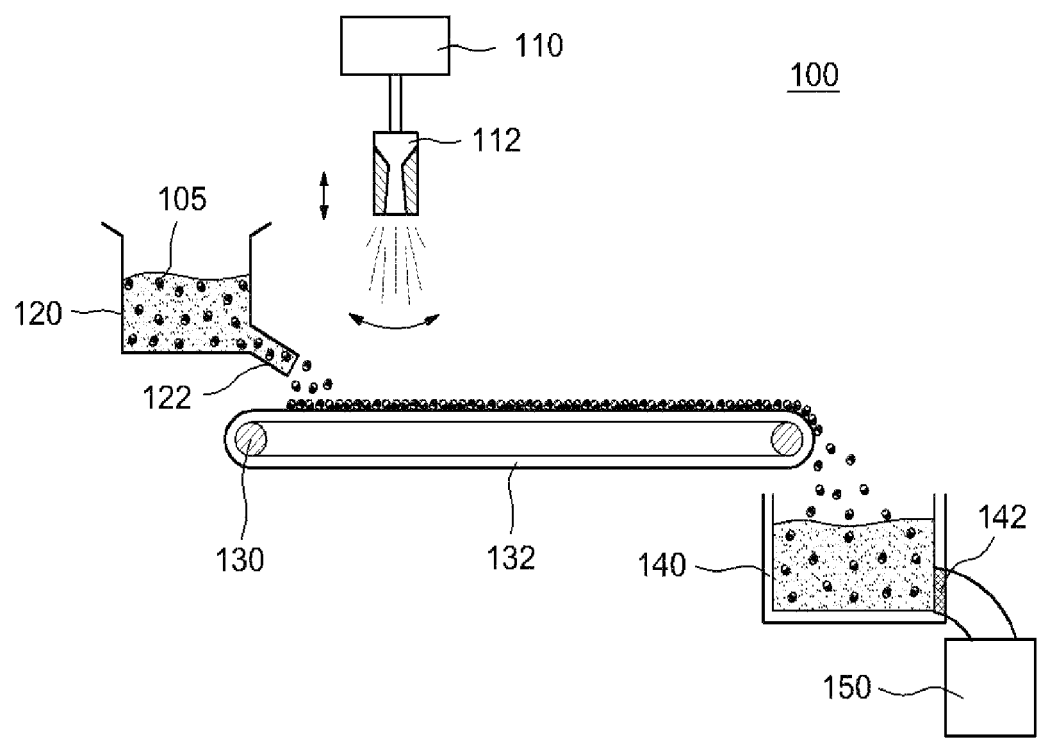
FIG. 1 shows an example of the apparatus that can treat the surface of sand with an etching solution in the method of manufacturing soil reinforced by microbe-based bio-binders in accordance with the present invention.

Desirable embodiments of the present invention are described below in detail in reference to the figures attached. As the present invention may evolve into various forms without departing from the main characteristics thereof, the scope of this invention is not limited to the below-described embodiments. Therefore, the embodiments of the present invention are provided to explain more explicitly this invention to a person or persons with appropriate knowledge.

The embodiments of this invention describe in detail the method of preparing the soil with urease-producing bacteria and polymer fibers which is not harmful to humans, does not cause environmental problems, and secures soil strength and resistance against wind. More specifically, they describe in detail the method of enhancing the soil strength with the fiber reinforcing effect provided by the polymer fibers which are mixed with the bio-binders. They also propose a method of eventually enhancing the strength of the bio-binders by increasing the adhesiveness of sand surface through a surface treatment.

The soil presented in this invention is defined as the soil which contains sand whose major components are silica and alumina, binders which bind the sand using urease-producing bacteria, and polymer fibers. As the objective of this invention is to improve the desert soil which are mainly consisted of silica and alumina, the soil strength and resistance against wind of the desert sand are increased by the binding potential and strength between the sand particles.

The sand applied in this invention is composed mainly of silica and alumina and the average diameter of sand particles is between 0.1 and 5 mm. The major components of silica and alumina imply that the combined weight accounts for more than 70% of the total.

The soil of this invention is prepared by binding ureolytic microbes, urea, reactants for calcium ion-containing binders, and polymer fibers to the sand whose major components are silica and alumina. The content of the polymer fibers in the sand ranges from 0.05 wt % to 5 wt %. Preferably, the microbes provide a $CaCO_3$ production rate of $1\sim 7\times 10^{-9}$ g $CaCO_3$ ppt cell$^{-1}$ hr$^{-1}$ under optimum conditions. The $CaCO_3$ production rate of this invention is the optimum value verified from the experiments for application of microbes to the soil. The typical product formed as $CaCO_3$ is calcite.

Out of the reactants composing binders of this invention, urease-producing bacteria form at least 33 g of calcite/liter when they are added to the sand. There are various methods to determine the content of calcite. One of the methods is to measure the carbon dioxide generated when the soil product is treated with an acid. The amount of carbon dioxide generated is determined by measuring the gas pressure change (manometer method) or the gas volume change. The amount of calcium carbonate present in the sample can be determined from the sample weight and the gas volume. Especially, two methods to determine the content of calcite can be found in the following reference (pages 206-210, Chapter 19. Soil Carbonate, Australian Laboratory Handbook of Soil and Water Methods by G. E. Raymond and F. R. Higginson, Onkata Press, 1992).

The microbes used in this invention can be those that produce urease and/or those that possess one or more characteristics allowing changes beneficial to application of the methods of this invention. In addition, the microbes can be those that can produce urease based on genetic mutation or genetic engineering and/or possess one or more characteristics allowing changes beneficial to application of the methods of this invention.

Preferable microbes come from Bacillacae family, more specifically from the list of species including *Bacillus, Sporosarcina, Sporolactobacillus, Clostridium* and *Desulfotomaculum*. More preferable microbes are *Sporosarcina pasteurii* or their functional equivalents. The functional equivalents of *Sporosarcina pasteurii* mean that the equivalents have at least one common property with *Sporosarcina pasteurii* and that they can be changed so as to be useful to the methods of this invention. A person or persons with adequate knowledge in this area can distinguish such bacteria. Of course, if necessary, combination of other microbes may be used.

Urea may be provided in a variety of forms, preferably in water-soluble solution. The calcium ion can exist in a variety of forms and may be provided in a form of a salt such as calcium chloride. However, at a higher concentration of urea, urease activity would be reduced due to the substrate inhibition.

The reactants may be added at the same time or in sequence. For example, urea and calcium ions, which can be added individually or pre-mixed, are applied to sand first, followed by microbes. Alternatively, urea and calcium ions at different conditions of this invention may be added sequentially or at the same time after microbes. The reactants can be added in various ways to the sand. The reactants may be added to sand under pressure by flushing, injecting, spraying, on-sand/in-sand dripping or trickling. Selectively, sand can be immersed into the reactants depending on the particle sizes.

The content of the polymer fibers added in this invention ranges 0.05 wt % to 5 wt % of the sand. If the content is less than 0.05 wt %, the fiber reinforcing effect may not be achieved. If it is greater than 5 wt %, the fibers may get entangled into a ball and the fiber reinforcing effect may not be embodied as desired in this invention. The content of polymer fibers can be determined considering the type and content of the sand depending on the conditions of the reinforced soil to be embodied. Here, the polymer fiber is synthetic (such as PP, HDPE) or bio-degradable fiber.

Bio-degradable fibers may be applied instead of the synthetic fibers of this invention. Biodegradable fibers refer to fibers that are mineralized through breakage of polymer chains by microbes and include polylactic acid (PLA) from corn or potato, recycled cellulose, milk-impregnated rayon, chitosan-mixed fibers, and rice straw. Among these, rice straw and chitosan-mixed fibers are preferable, with the rice straw being more preferable.

The strengths of soil were measured by triaxial compression tests. In the triaxial compression test, cylindrical soil samples are inserted into a pressure chamber and compressed by a liquid horizontally and by an external load vertically to measure the stress and strain at shear failure which allows the determination of the angle of friction and cohesion of the soil. The soil strength by the angle of friction was measured in this invention. In addition, resistance against wind was determined by the wind erosion test in which the amount of mass loss from the soil of this invention by artificial wind was measured in g/cm$^2$.

Selectively, the soil strength can be enhanced in this invention. In the embodiments of this invention, the methods of etching sand or treating the surface of the sand by spraying are proposed. The surface-treated sand may be mixed in a certain ratio with sand with no surface treatment in consideration of the soil strength and the cost required for surface treatment.

The etching method can be implemented preferably by contacting directly an etching solution to the surface of sand or by using plasma. The direct contact method can be implemented by spraying the etching solution on sand or by submerging sand in the solution for a certain period of time.

Plasma can improve the surface tension, adhesion and viscosity. Thus, any plasma method that can create defects on the sand surface can be utilized. The plasma treatment method is classified in principle into the vacuum treatment method and the atmospheric treatment method of treating boards under atmospheric pressure. The plasma treatment of this invention includes the reactive ion etching method. Especially, since the major component of sand for this invention is $SiO_2$ or $SiO_2/Al_2O_3$ mixture, CFx gases are preferable as reactive gases forming plasma.

In the vacuum plasma treatment method, sand is introduced into a chamber under vacuum or at a low pressure in which ions and electrons formed through plasma ionization process treat boards by using electrically-neutral but chemically very reactive radicals generated through dissociation. The source of the plasma may be either direct plasma or remote plasma. In the atmospheric plasma treatment method, the formed plasma source is induced to the outside of the equipment for contact with boards under atmospheric pressure to provide the necessary plasma treatment. Detailed description of the plasma treatment is omitted here, since the treatment method is well known.

FIG. 1 shows an example of a piece of equipment (100) for treating the sand surface with an etching solution in manufacturing soil reinforced by microbe-based bio-binders according to the embodiments of this invention. In this figure, the method of spraying the etching solution is presented, which is one of many possible etching methods.

As shown in FIG. 1, the equipment 100 of etching the sand surface is mainly composed of a sand-supplying part, an etching solution spraying part, a fed-sand transferring part, an etching solution/sand recovery part. Each of the component parts is presented here to describe conceptually the etching equipment 100 of this invention and therefore a variety of methods may be added in real applications to optimize the operation of each component part. For example, a vibrator may be added to the sand transfer part to spray the etching solution on sand more uniformly through vibration.

The sand 105 supplying part includes the sand storage tank 120 and sand feeding entrance 122. The etching solution spraying part includes the etching solution storage tank 110 and the etching solution spraying nozzle 112. The sand transfer part transfers the sand to the belt 132 by means of rollers 130. The recovery part is composed of the mixing tank 140 to recover the mixture of etching solution/sand and the filter 142 installed at the mixing tank to separate the etching solution. The etching solution filtered through the filter is recovered in the separate etching solution recovery tank 150.

The etching solution spraying nozzle 110 moves or rotates left/right or upward/downward so that the etching solution may be applied to transferring sand uniformly. The fed sand may be transferred continuously or stepwise in consideration of the degree of etching on the sand surface and the amount of the fed sand.

In the spraying method, spraying powder is sprayed under acceleration at non-molten state for attachment on the sand surface by compressed gas. The spraying powder may be a component to enlarge the specific surface area of sand or increase the surface roughness. Thus, such functional particles may be silver nano particles for antifungal function or titanium dioxide particles for photo-catalyst function, or a mixture of the two. The particles providing specific functions are called functional particles.

Figure 2:
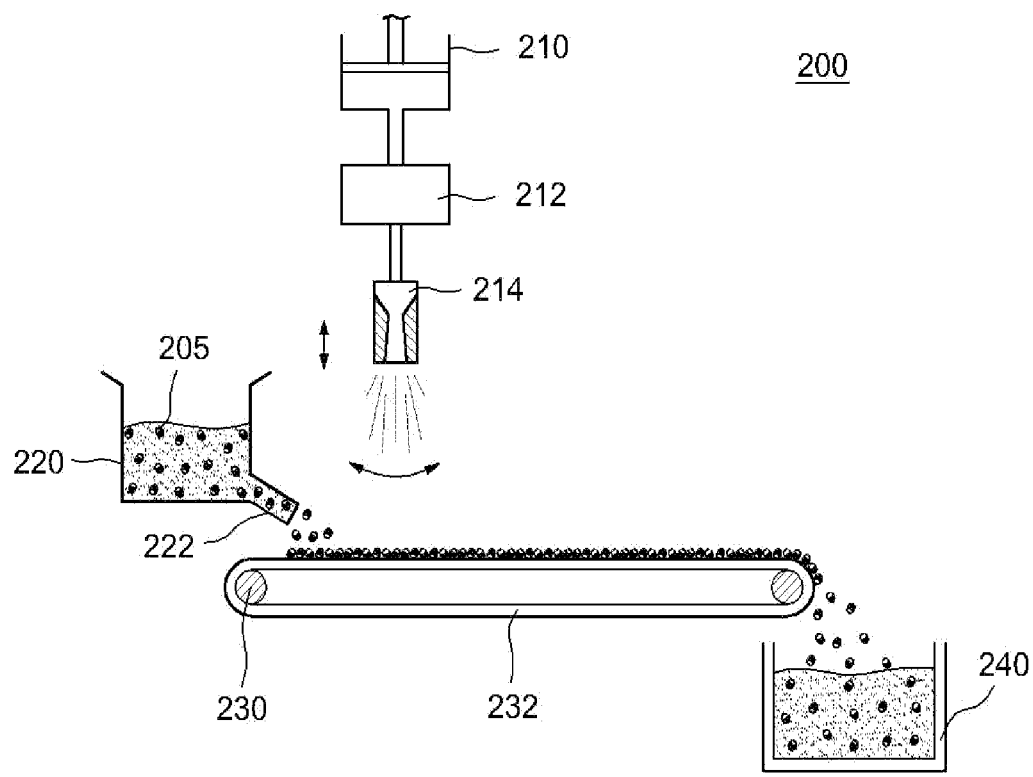
FIG. 2 shows an example of the apparatus that can treat the surface of sand by spraying in the method of manufacturing soil reinforced by microbe-based bio-binders in the present invention.

FIG. 2 shows an example of a piece of equipment 200 for treating the sand surface with a spraying method in manufacturing soil reinforced by microbe-based bio-binders according to the embodiments of this invention.

As shown in FIG. 2, the equipment 200 of treating the sand surface with powder is largely divided into a sand supplying part, a powder spraying part, a fed-sand transferring part, and a powder-treated sand recovery part. Each the components are presented here to describe conceptually the powder treatment equipment 200 of this invention and therefore a variety of methods may be added in real applications to optimize the operation of each component part. For example, a vibrator may be added to the sand transfer part to spray the powder on sand more uniformly through vibration.

The sand 205 supplying part 205 includes the sand storage tank 220 and sand feeding entrance 222. The powder spraying part is composed of the powder storage tank 212, powder spraying nozzle 214 and the pressurizing part 210 of increasing the kinetic energy of powder by supplying pressure or pressure/heat. The sand transfer part transfers the sand to the moving belt 232 by rollers 230. The sand surface-treated by the powder is recovered in the recovery tank 240.

The powder spraying nozzle 214 moves or rotates left/right or upward/downward so that the powder may be applied to transferring sand uniformly. The fed sand may be transferred continuously or stepwise in consideration of the degree of surface treatment by the spraying powder and the amount of fed sand. The surface of sand treated by the powder may be partly damaged or partly plugged by the powder.

Embodiment 1

A urea-NB medium (20 g urea and 3 g nutrient broth per 1 L of distilled water) was prepared by autoclaving, to which filter-sterilized 1 M $CaCl_2$ was added to a final concentration of 100 mM $CaCl_2$. Then, *S. pasteurii* (American Type Culture Collection 11859) was asceptically suspended to the urea-NB-$CaCl_2$ medium to obtain a concentration of $1\times10^7$ cells/mL. For the soil tests, the medium with cells and sand were mixed together at a ratio of 15 ml to 100 g, to which 0.25 g of polypropylene fibers (5 cm in length, 1.2 mm in width, and 0.038 mm in thickness) were mixed thoroughly to assure an even distribution of sand, cells, and fibers in the mixture. The mixture was transferred to the experimental apparatus and placed in an oven at 45° C. for four days before being tested.

Later, with the tri-axial compression test (GEOTAC sigma-1), the soil strength of 7-cm-diameter 18 cm-length 155 $kg/m^3$-weight soil was measured to be 2,250 psf at a strain rate of 1.25 mm/min.

Embodiments 2~3

All conditions were the same as those of Embodiment 1 except for the amounts of polypropylene fibers of 2 g and 4.5 g for examples 2 and 3, respectively, and the soil strengths were measured.

Embodiments 4~6

All conditions were the same as those of Embodiments 1 through 3 except for the use of rice straw instead of the synthetic polypropylene fibers and the soil strengths were measured in the same way as Embodiment 1.

Embodiments 7~9

All conditions were the same as those of Embodiments 1 through 3 except for the use of chitosan instead of the synthetic polypropylene fibers and the soil strengths were measured in the same way as Embodiment 1.

Embodiments 10~12

All conditions were the same as those of Embodiments of 1 through 3, but sand was surface-treated as explained in Table 1, using the etching solution of $C_2F_6$ Embodiments 13~15

All conditions were the same as those of Embodiments of 1 through 3, but sand was surface-treated as explained in Table 2. Specifically, sand powder with an average particle size of 0.4 mm ($SiO_2/Al_2O_3$, major component) was prepared and sprayed on the sand surface by using compressed air of 30 atm pressure. and 380° C. with the standard laval type spray nozzle with an aperture of 4×6 mm and a throat gap of 1 mm.

Comparative Example 1

A urea-NB medium (20 g urea and 3 g nutrient broth per 1 L of distilled water) was prepared by autoclaving, to which filter-sterilized 1 M $CaCl_2$ was added to a final concentration of 100 mM $CaCl_2$. Then, *S. pasteurii* (American Type Culture Collection 11859) was aseptically suspended to the urea-NB-$CaCl_2$ medium to obtain a concentration of $1 \times 10^7$ cells/mL. For the soil tests, the medium with cells and sand were mixed together at a ratio of 15 ml to 100 g thoroughly to assure an even distribution of sand and cells in the mixture. The mixture was transferred to the experimental apparatus and placed in an oven at 45° C. for four days before being tested.

Later, with the tri-axial compression test and wind erosion test, the soil strengths and weight losses were measured.

Comparative Examples 2~6

All conditions were the same as those of Embodiments 1, 4, 7, 10 and 13 except for the addition of 5.5 g of each relevant polymer fibers to the sand. Table 1 describes the soil strength relationship between the soil reinforced by microbe-based bio-binders according to the embodiments of this invention and the soil not containing polymer fibers as shown in comparative example 1. The strength ratio means the soil strength ratio of each reinforced soil to sand only. The angle of friction for sand only was 27.9°.

| Classification | Polymer Fiber (g/sand 100 g) | Soil Strength Friction Angle (Φ) | Strength Ratio |
|---|---|---|---|
| Embodiment 1 | PP | 0.25 | 39.2° ± 0.25 | 1.54 |
| Embodiment 2 | | 2 | 40.1° ± 0.25 | 1.59 |
| Embodiment 3 | | 4.5 | 39.1° ± 0.25 | 1.53 |
| Embodiment 4 | Rice Straw | 0.25 | 37.3° ± 0.25 | 1.44 |
| Embodiment 5 | | 2 | 38.1° ± 0.25 | 1.48 |
| Embodiment 6 | | 4.5 | 37.1° ± 0.25 | 1.43 |
| Embodiment 7 | Fibers containing Chitosan | 0.25 | 36.4° ± 0.25 | 1.39 |
| Embodiment 8 | | 2 | 37.3° ± 0.25 | 1.44 |
| Embodiment 9 | | 4.5 | 36.2° ± 0.25 | 1.38 |
| Embodiment 10 | PP with surface treated with etching solution | 0.25 | 40.0° ± 0.25 | 1.58 |
| Embodiment 11 | | 2 | 40.9° ± 0.25 | 1.63 |
| Embodiment 12 | | 4.5 | 39.9° ± 0.25 | 1.58 |
| Embodiment 13 | PP with surface treated with spraying method | 0.25 | 40.8° ± 0.25 | 1.63 |
| Embodiment 14 | | 2 | 41.5° ± 0.25 | 1.67 |
| Embodiment 15 | | 4.5 | 40.6° ± 0.25 | 1.62 |
| Cmp. Example 1 | / | | 30.0° ± 0.25 | 1.09 |
| Cmp. Example 2 | PP | 5.5 | 31.3° ± 0.25 | 1.15 |
| Cmp. Example 3 | Rice Straw | 5.5 | 30.9° ± 0.25 | 1.13 |
| Cmp. Example 4 | Chitosan cnt'd | 5.5 | 30.8° ± 0.25 | 1.26 |
| Cmp. Example 5 | PP | 5.5 | 32.6° ± 0.25 | 1.20 |
| Cmp. Example 6 | PP | 5.5 | 32.8° ± 0.25 | 1.21 |

* Cmp: comparative

According to Table 1, the soil reinforced by microbe-based bio-binders without polymer fibers has 1.09 times the soil strength of the soil composed of sand only. Like embodiments 1 through 3, however, the soil mixed with synthetic polypropylene (PP) fibers showed 1.53 to 1.59 times the soil strength of the soil composed of sand only. Thus, blending PP fibers was found to increase the soil strength remarkably over the case without the fibers.

Similarly, embodiments 4 through 6 in which rice straw was mixed instead of PP fibers and embodiments 7 through 9 in which chitosan was mixed also show that the fiber reinforcing effect is remarkable. In addition, the surface treatment improved the soil strength as shown by embodiments 10 through 12 in which the surface was treated with the etching solution and embodiments 13 through 15 in which the surface was treated with the spraying method. The surface treatment was found to be desirable in order to increase the binding force between sand particles whose main components are silica and alumina have relatively weak surface friction.

According to comparative examples 2 through 6 in which 5.5 wt % of polymer fibers were mixed, the soil strength ratios were found to be only 1.13 to 1.26. As shown in comparative example 1, the soil composed of sand and bio-binders did not improve the soil strength much over the soil composed of sand only, compared with the soil in embodiments of this invention. In other words, if the content of polymer fibers is greater than 5 wt % the polymer fibers may get entangled themselves to form a ball, which loses the fiber reinforcing effect to be embodied in this invention.

Embodiments 16~18

A urea-NB medium (20 g urea and 3 g nutrient broth per 1 L of distilled water) was prepared by autoclaving, to which filter-sterilized 1 M $CaCl_2$ was added to a final concentration of 100 mM $CaCl_2$. Then, *S. pasteurii* was aseptically suspended to the urea-NB-$CaCl_2$ medium to obtain a concentration of $1 \times 10^7$ cells/mL. For the soil tests, the medium with cells and sand were mixed together at 0.05, 0.1, 0.5, 1, 2, 3, 5, and 10 ml per 100 g, to which 0.25 g of polypropylene fibers (5 cm in length, 1.2 mm in width, and 0.038 mm in thickness) were mixed thoroughly to assure an even distribution of sand, cells, and fibers in the mixture. The mixture was transferred to the experimental apparatus and placed in an oven at 45° C. for four days before being tested.

Later, it was exposed to wind with velocities of 32, 48 and 64 km/hr to measure the amount of sand lost.

Comparative Examples 7~9

In these examples, the amount of sand weight loss was measured for the soil which had been prepared without adding the PP fibers with the rest of conditions same as those of embodiments 16 through 18.

Table 2 describes the weight loss relationship between the soil reinforced by microbe-based bio-binders according to the embodiments of this invention and the soil reinforced by microbe-based bio-binders but not containing synthetic fibers as shown in comparative examples 7, 8, and 9.

| Classification | Fiber | Wind Velocity (km/hr) | Weight Loss (g/cm²) to Reactants(mL/sand 100 g) | | | | | | | |
|---|---|---|---|---|---|---|---|---|---|---|
| | | | 0.05 mL | 0.1 mL | 0.5 mL | 1.0 mL | 2.0 mL | 3.0 mL | 5.0 mL | 10.0 mL |
| Embodiment 16 | PP | 32 | 0.208 | 0.141 | 0.017 | 0 | 0 | 0 | 0 | 0 |
| Embodiment 17 | | 48 | 0.321 | 0.290 | 0.271 | 0 | 0 | 0 | 0 | 0 |
| Embodiment 18 | | 64 | 0.770 | 0.648 | 0.538 | 0 | 0 | 0 | 0 | 0 |
| Cmp. Example 7 | / | 32 | 0.260 | 0.184 | 0.020 | 0.006 | 0 | 0 | 0 | 0 |
| Cmp. Example 8 | | 48 | 0.846 | 0.778 | 0.620 | 0.164 | 0.020 | 0.002 | 0 | 0 |
| Cmp. Example 9 | | 64 | 1.420 | 1.364 | 0.989 | 0.522 | 0.006 | 0.008 | 0 | 0 |

* Cmp: Comparative

According to Table 2, as shown in embodiments 16 through 18 in which PP fibers were added to soil, no sand was lost against the wind velocities of 32, 48 and 64 km/hr even though 1 mL of reactants was mixed with 100 gram of sand. In contrast to this, in comparative examples 7 and 8 in which no PP fibers were added to the soil, at least 2 mL of bio-binders was needed against the wind velocity of 32 km/hr, at least 5 mL against the wind velocity of 48 km/hr, and at least 5 mL against the wind velocity of 64 km/hr. In other words, if polymer fibers such as PP fibers were not added, the amount of bio-binders required to resist the wind increased with the increase in wind velocity.

The bio-binders applied to this invention are relatively expensive. Thus, it is imperative to obtain desirable wind resistance with as little amount of bio-binders as possible. According to embodiments 16 through 18, if the soil is reinforced with polymer fibers, the dramatically increased resistance against wind can reduce the amount of expensive bio-binders. Especially, the addition of polymer fibers can reduce the amount of bio-binders needed to be added to prevent the yellow sand phenomenon of flying sand in arid areas.

According to the method of manufacturing soil reinforced by microbe-based bio-binders and the soil produced by such method, soil that is not harmful to humans, doesn't cause environmental pollution, and secures sufficient soil strength and resistance against wind can be prepared by using urease-producing bacteria and polymer fibers.

As mentioned above, even though this invention is explained in detail through embodiments, this invention is not limited to the embodiments and therefore it is possible to create different variations that are within the technical realms of this invention by a person or persons with adequate knowledge in the pertinent field.

| * Explanation of referring number | |
|---|---|
| 100: etching equipment, | 1100: etching solution storage tank |
| 112, 2140: spraying nozzle, | 1200: sand storage tank |
| 1220: sand feeding entrance, | 130, 2300: rollers |
| 132, 2320: belt, | 1400: mixing tank |
| 1420: filter, | 1500: etching solution recovery tank |
| 2120: powder storage tank, | 2400: recovery tank |

The invention claimed is:

1. A method of manufacturing a soil reinforced by microbe-based bio-binders and having a polymer fiber content ranging from 0.05 wt % to 5 wt %, comprising the steps of:
    preparing a sand whose major components are silica and alumina;
    treating a surface of the sand by blowing functional-particles using a compressed gas so as to increase a specific surface area of the sand or a surface roughness of the sand; and
    binding urea-producing microbes, urea, calcium ion and the polymer fibers to the sand, wherein the microbes are characterized to produce $CaCO_3$ at a rate of $1\sim7\times10^{-9}$ g $CaCO_3$ ppt $cell^{-1}$ $hr^{-1}$,
    wherein the functional-particles include silver-nano particles, titanium dioxide particles, a sand powder or a mixture thereof.

2. The method of claim 1, wherein the urea-producing microbes are one or more selected from the group consisting of *Bacillus, Sporosarcina, Sporolactobacillus, Clostridium* and *Desulfotomaculum.*

3. The method of claim 1, wherein the urea-producing microbes are one or more selected from the group consisting of *Sporosarcina pasteurii* and their functional equivalents.

4. The method of claim 1, wherein the polymer fibers are bio-degradable fibers.

5. The method of claim 4, wherein the bio-degradable fibers are one or more selected from the group consisting of Polylactic acid (PLA), Cellulose, milk-invaginated rayon, chitosan-mixed fibers, and rice straw.

* * * * *